United States Patent [19]

Petersen et al.

[11] Patent Number: 4,739,273
[45] Date of Patent: * Apr. 19, 1988

[54] APPARATUS FOR DETECTING SUBSTANTIALLY LONGITUDINAL FLAWS IN THE END AREA OF A TUBULAR MEMBER USING MAGNETIC EXCITATION AND A SCANNING SENSOR

[75] Inventors: Clifford W. Petersen; Mark C. Moyer, both of Missouri City, Tex.

[73] Assignee: Exxon Production Research Company, Houston, Tex.

[*] Notice: The portion of the term of this patent subsequent to Mar. 5, 2002 has been disclaimed.

[21] Appl. No.: 585,686

[22] Filed: Mar. 2, 1984

[51] Int. Cl.⁴ .................. G01N 27/72; G01R 33/12
[52] U.S. Cl. ................................. 324/242; 324/235; 324/262
[58] Field of Search ............... 324/239, 243, 227, 235, 324/262

[56] References Cited

U.S. PATENT DOCUMENTS

| | | | |
|---|---|---|---|
| 3,327,205 | 6/1967 | Wood et al. | 324/220 |
| 3,483,466 | 12/1969 | Crouch et al. | 324/220 |
| 3,535,624 | 10/1970 | Wood | 324/226 |
| 3,539,915 | 11/1970 | Walters et al. | 324/220 |
| 3,710,236 | 1/1973 | Halsey et al. | 324/227 |
| 3,753,085 | 8/1973 | Morton et al. | 324/226 |
| 3,906,357 | 9/1975 | Runshang | 324/226 |
| 4,218,615 | 8/1980 | Ivy | 324/227 |
| 4,258,318 | 3/1981 | Furukawa et al. | 324/220 |
| 4,503,393 | 3/1985 | Moyer et al. | 324/235 |

OTHER PUBLICATIONS

Moyer et al., "An Automated . . . Device . . . Drill String" Feb. 1983 Drilling Conference Reprint. IDAC/SPE 1983 pp. 301-306.
Stanley et al., "OCTG Inspection Procedures Reviewed . . ." Oil and Gas Journal, 11/1983, pp.-99-104.

Primary Examiner—Reinhard J. Eisenzopf
Assistant Examiner—Walter E. Snow
Attorney, Agent, or Firm—Mitchell D. Lukin

[57] ABSTRACT

An apparatus for detecting substantially longitudinal flaws in the end area of a tubular member is disclosed. The apparatus comprises magnetizing-detection units, means for moving-said units along a helical path about the surface of the end area of the tubular member, and means for centralizing and securing the apparatus on the end of the tubular member being inspected. Magnetic detection transducers on the magnetizing-detection units detect perturbations in the applied magnetic field in the area of any substantially longitudinal flaws. The magnetic detection transducers are mounted so as to remain remote from the surface of the tubular member during operation of the apparatus. The field is generated in the tubular member by said magnetizing-detection units. The magnetizing-detection units are pivotably mounted to allow for movement over both flat and tapered surfaces. The signals generated by the magnetic detection transducers are transmitted to an external indicating device through slip rings.

26 Claims, 3 Drawing Sheets

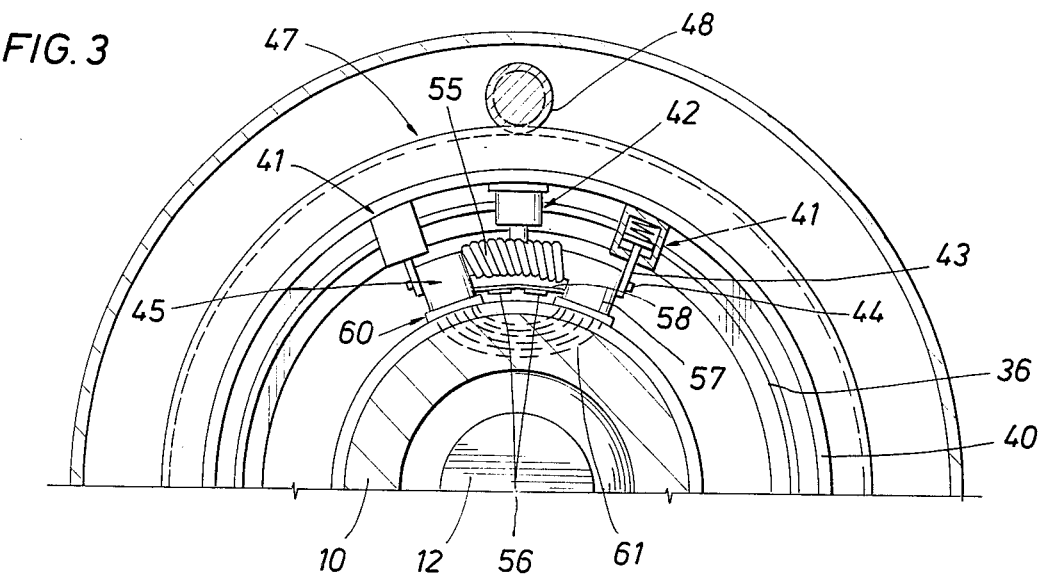
FIG. 3
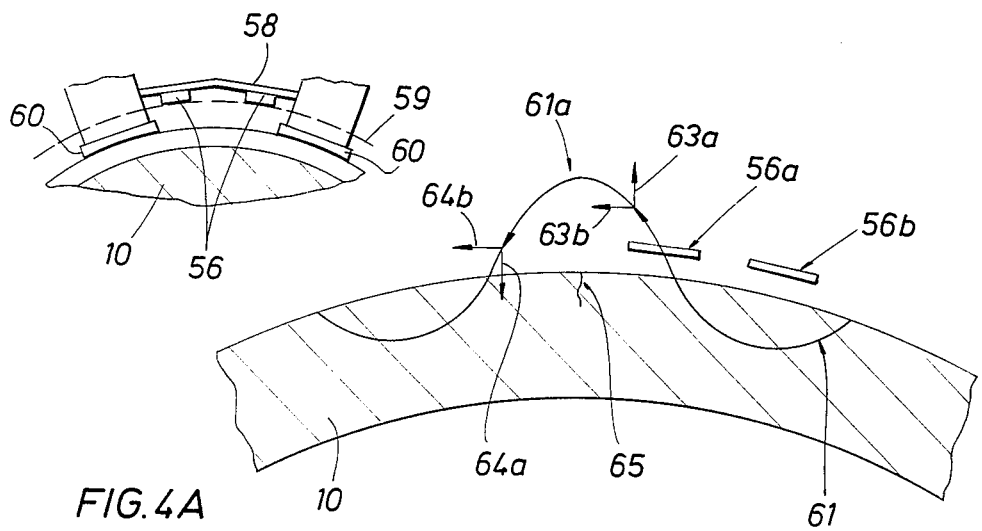
FIG. 3A
FIG. 4A
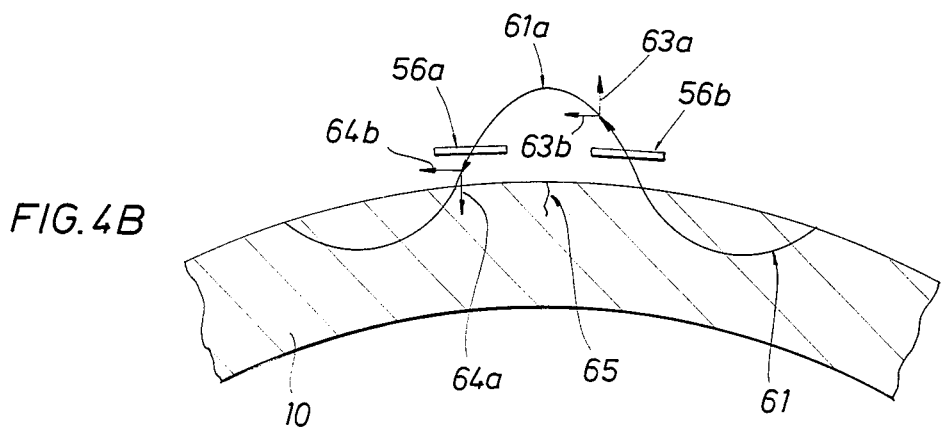
FIG. 4B

4,739,273

APPARATUS FOR DETECTING SUBSTANTIALLY LONGITUDINAL FLAWS IN THE END AREA OF A TUBULAR MEMBER USING MAGNETIC EXCITATION AND A SCANNING SENSOR

FIELD OF THE INVENTION

This invention relates to an apparatus for detecting substantially longitudinal flaws in the end areas of tubular members by detecting radial anomalies in an applied magnetic field, and is particularly suited to detecting such flaws in the end areas of threaded tubular members.

BACKGROUND OF THE INVENTION

Casing and tubing failures are a source of great concern to producers of oil and gas. During the drilling of oil and gas wells, at least a portion of the well is lined with a tubular casing. Drilling fluids are circulated for various purposes through the drill string and back to the surface through the casing. Failure of this casing will allow undesirable leakage of drilling fluids into surrounding formations.

A more serious problem may result from the failure of production tubing. Tubing runs from the producing formation downhole up to the wellhead. If the tubing fails, the gas or oil being produced may leak to the surface along the outside of the tubing, and thence into the atmosphere, creating a risk of explosion or fire. In the case of subsea wells, the leakage may flow into the water causing serious pollution.

Many of the failures of casing and tubing are caused by longitudinal manufacturing flaws, such as laps, seams and plug scores, or from service induced defects such as caliper tracks. As such, it is not unusual for each length of casing or tubing to be inspected prior to installation in a well. Although inspection of the shank portion of tubing and casing is relatively straightforward, the inspection of the end areas of tubing and casing is not as simple. These ends are often "upset" (manufactured so that the wall of the tubular product is of extra thickness and strength near the end) and threaded. Currently, the magnetic particle inspection method is the primary method used for such end area inspections. In this method, the area to be inspected is magnetized and then dusted with fine particles of iron or iron oxide. These particles accumulate in the presence of cracks, thus giving a visual indication of the location of any flaws. This method is limited in that the area to be inspected must be thoroughly cleaned before the inspection. The method is also dependent on the alertness and visual acuity of the inspector.

A better method for detecting flaws at the end areas of tubular products makes use of magnetically sensitive transducers to detect flaws. A system of this type is described in U.S. patent application Ser. No. 308,749, filed on Oct. 5, 1981 by Moyer et al., the entirety of which is incorporated by reference. The apparatus described therein comprises an apparatus for applying a magnetic force to produce a generally axial field through the threaded end of a pipe and having various means for sensing radial magnetic fields and generating signals corresponding to those magnetic fields. Substantially transverse flaws in the pipe cause discontinuities in the magnetic flux lines which are generated in the pipe. These discontinuities in the magnetic field are detected by the sensing elements. The apparatus is not designed to detect the substantially longitudinal flaws often found in tubing and casing.

Another apparatus for detecting flaws on the ends of tubular products is disclosed in U.S. Pat. No. 3,710,236, issued Jan. 9, 1973 to H. P. Halsey et al. Halsey et al. disclose an apparatus for detecting longitudinal flaws in a magnetically energized body using a pair of overlaying, overlapping Hall devices. The apparatus includes a mounting assembly for fixedly positioning the Hall devices at the proper angle relative to the pipe. Should the body being inspected have both straight and tapered surfaces, the device mounting must be readjusted for inspection of the different surfaces. This apparatus provides no means for mechanically engaging the body being inspected and automatically moving the Hall devices about the end area of the body so as to scan the entire end area.

SUMMARY OF THE INVENTION

The present invention is an apparatus for detecting substantially longitudinal flaws in the end areas of a tubular member. The apparatus comprises combination magnetizing-detection units, means for rotating said units along a helical path about the surface of the tubular member, and means for centralizing and securing the apparatus on the end of the tubular member being inspected, all mounted in a frame.

The magnetizing-detection units comprise a magnetizing yoke and magnetic detection transducers. The magnetizing yoke is designed to provide a localized, generally circumferential magnetic field through a portion of the tubular member. The field is sufficiently large to enable detection of defects. The magnetic detection transducers are mounted so as to remain remote from the surface of the tubular member during operation of the apparatus. The magnetic detection transducers generate a signal in response to the component of magnetic flux normal to the surface of the tubular member. The magnetizing-detection units are pivotably mounted to allow for movement over tapered or straight surfaces. The signals from these transducers are electronically amplified, and transmitted through slip rings to an external indicating device. The signals may then be differentially processed to highlight defect discrimination and reduce irrelevant background indications.

BRIEF DESCRIPTION OF THE DRAWINGS

FIG. 3 is a sectional view taken along lines 3—3 of FIG. 1.

FIG. 3A is a detailed view showing the orientation of the magnetic detection transducers relative to a casing during inspection operations.

FIGS. 4A and 4B are a schematic sectional view of the magnetizing-detection units of FIG. 1 shown in operation.

DETAILED DESCRIPTION OF THE INVENTION

The flaw detection apparatus of the present invention, in its preferred embodiment, comprises a combination magnetizing portion with one or more magnetizing-detection units, means for moving those units about the outer surface of a tubular member, and a means for centralizing and securing the apparatus on the tubular member, all of which will be described in more detail below.

Figure 1:
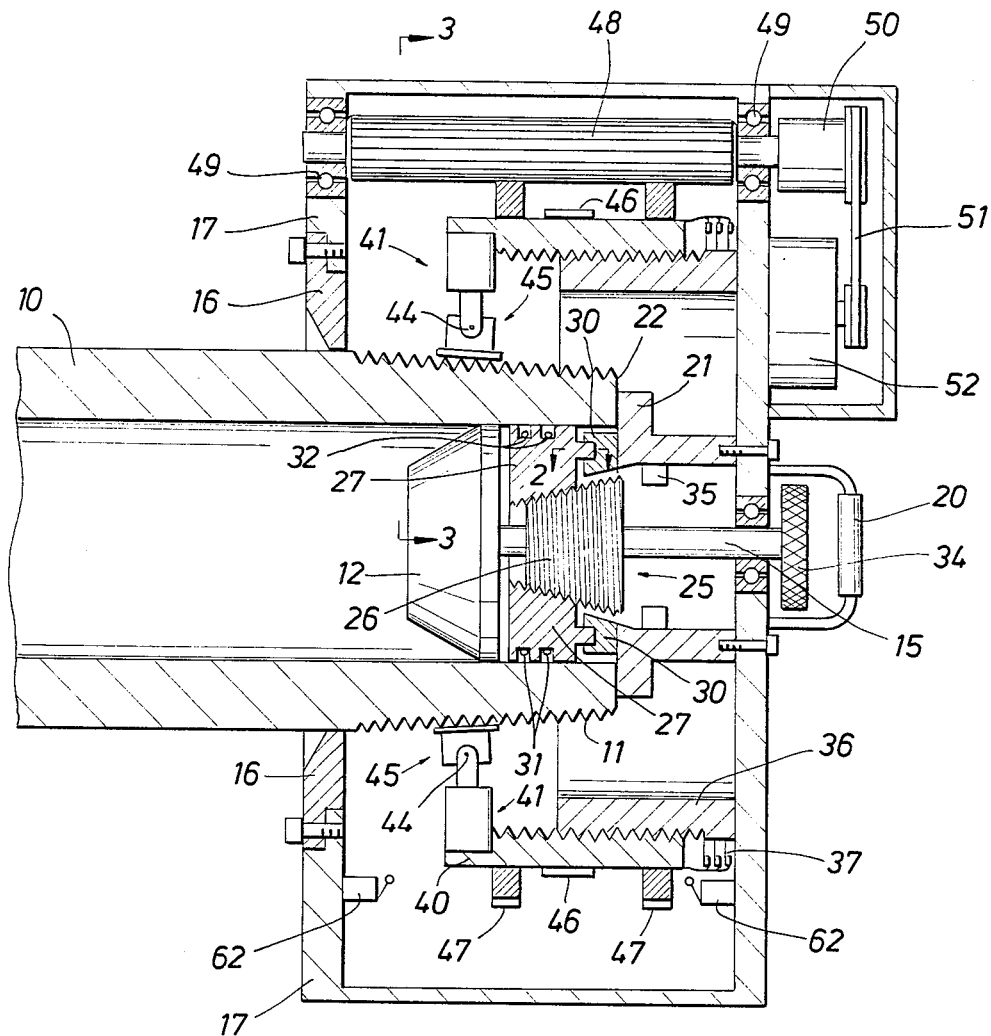
FIG. 1 is a sectional view of the apparatus of the present invention mounted on a casing for inspection.

Referring now to FIG. 1, the apparatus is shown mounted on a tubular member, casing 10. Casing 10 is shown here as having external threads 11. Casing 10 may also be tubing, drill pipe, or any other tubular member, with or without threads.

The flaw detection apparatus is held in place to allow its operation by the centralizing and securing means. Centralizing guide piston 12 is fixedly attached to the end of shaft 15. The apparatus is mounted on the casing to be inspected by inserting guide piston 12 into the bore of the casing. Elastomeric guide 16 is attached to main assembly frame 17 to assist in positioning the apparatus on casing 10. Handle 20 is mounted on frame 17 to assist in lifting the apparatus and placing it onto the end of the casing. By pushing on handle 20, the flaw detection apparatus is moved onto the end of the casing until mechanical stops 21 lodge against the end 22 of the casing.

Figure 2:
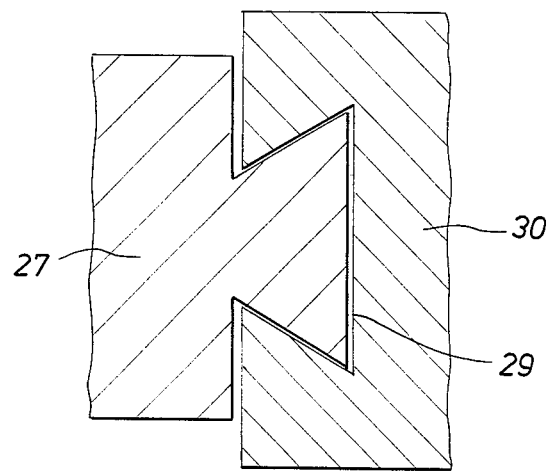
FIG. 2 is a sectional view taken along lines 2—2 of FIG. 1.

The flaw detection apparatus is secured in place on the casing using expandable wedge assembly 25, details of which are shown in FIGS. 1 and 2. Wedge assembly 25 comprises a frustoconical inner element 26 having a threaded outer surface and a plurality of outer elements 27 equally spaced about inner element 26. Inner element 26 is fixedly mounted on shaft 15.

Outer elements 27 have a threaded surface which mates with the threaded outer surface of inner element 26. Outer elements 27 are slideably mounted in dovetail grooves 29 (FIG. 2) on extension brackets 30 so as to be slidable in the radial direction. Elastomeric bands 31 mounted in grooves 32 encircle the outer elements 27. These bands 31 serve to keep outer elements 27 engaged with the threads of inner element 26 when the flaw detection apparatus is not secured to the casing.

When wheel 34, which is fixedly attached to shaft 15, is rotated, the threaded outer surface of inner element 26 interacts with the threaded surface of each outer element 27, forcing the outer elements outward against the inner surface of casing 10. The slidable mounting of outer elements 27 in grooves 29 (FIG. 2) allow these elements to move radially outward against the inner surface of casing 10, while preventing outer elements 27 from rotating when inner element 26 is rotated.

When the apparatus is to be withdrawn from the casing, wheel 34 is rotated in the opposite direction. As inner element 26 moves outward within the casing bore, elastomeric bands 31 force outer elements 27 radially inward so as to no longer be in contact with the inner surface of casing 10, thus allowing the flaw detection apparatus to be moved. Stops 35 are provided so that inner element 26 may not be completely disengaged from outer elements 27 unless elastomeric bands 31 are removed.

A cylindrical inner support bracket 36 is affixed to the inner surface of frame 17. A portion of the outer surface of this cylindrical bracket is threaded. Slip rings 37, whose function are discussed below, are mounted on the unthreaded portion of the outer surface of inner support bracket 36. A second or outer cylindrical support 40 having a threaded inner surface is threaded onto support bracket 36. Spring pistons 41 and electric solenoid 42 (FIG. 3) for magnetizing-detection units 45 are mounted on outer support 40. Electronic amplifiers 46 are shown mounted on outer support 40, although they may also be mounted elsewhere in the flaw detection apparatus. These elements will be discussed in more detail below.

As shown in FIG. 1, means are provided for moving the magnetizing-detection units 45 about the surface of casing 10. Two ring gears 47 are mounted about the outer surface of outer support 40. These gears are arranged to mesh with drive pinion gear 48. Drive pinion gear 48 is rotatably mounted in bearings 49 on frame 17. Pinion gear 48 is driven through clutch 50 and belt 51 by adjustable speed, reversible electric motor 52. The adjustable speed motor is necessary if the same apparatus is to be used on different sizes of casing. The rotational speed may be adjusted so that the speed of the magnetizing-detection units relative to the surface is the same regardless of the casing diameter. As noted below, the speed adjustment may also be used to increase the defect sensitivity of the apparatus.

As shown in FIG. 3, magnetizing-detection units 45, two of which are included in the preferred embodiment (only one shown), are attached to outer support 40 by spring pistons 41. Magnetizing-detection unit 45 is pivotably connected to plunger and spring assembly 43 of each spring piston 41 at pin 44. Spring pistons 41 exert a force pulling the magnetizing-detection unit 45 radially away from casing 10. Electric solenoid 42, when energized, pushes against magnetizing-detection unit 45. The magnetizing-detection unit is thus pushed radially inward, against the force of spring pistons 41, into contact with the casing surface for inspection operations. When solenoid 42 is de-energized, spring pistons 41 pull the magnetizing-detection unit away from the casing. Because magnetizing-detection unit 45 is pivotably mounted at pins 44, magnetizing-detection unit 45 may pivot about the fulcrum where solenoid 42 pushes against the magnetizing-detection unit when that solenoid is energized. The maximum amount of pivot is controlled by stops (not shown), so that the magnetizing-detection units will remain generally in a proper orientation relative to the casing when solenoid 42 is not energized. The pivotable attachment makes the magnetizing-detection unit essentially self-aligning to tapered or straight surfaces, allowing the magnetizing-detection unit to maintain effective contact with the casing over both tapered and straight portions of the end area of the casing during inspection operations.

Each magnetizing-detection unit 45 comprises a magnetizing yoke and two magnetic detection transducers 56. The magnetizing yoke comprises a U-shaped steel core 57 (which may be laminated) having a coil 55 wrapped about the portion of the core between the two legs. Alternatively, the magnetic yoke may comprise a U-shaped permanent magnet. The yoke is aligned so that the magnetic flux passing between the two legs of the core passes through the casing generally circumferentially in a plane substantially perpendicular to the longitudinal axis of the casing.

The two magnetic detection transducers 56 are preferably Hall element devices, and are mounted on support 58 between the two legs of core 57. The transducers are mounted so that when the apparatus is in operation, the transducers will remain offset or remote from the surface of the casing. This prevents damage to the transducers which might be caused by contact with surface defects, and eliminates wear which would be caused by contact with the casing. The transducers are positioned on support 58 such that an imaginary surface 59 (FIG. 3A) passing through the surface of each of the two transducers is substantially concentric to the outer surface of the casing. The two transducers thus mounted are substantially equidistant from the surface of casing 10. The advantage of this equidistant mounting will be discussed below.

In the preferred embodiment, the transducers are spaced about one-eighth inch apart and are aligned such that the line passing through the center line of each transducer is substantially perpendicular to the longitudinal axis of the casing. This spacing is optimal for detecting a notch having a depth of 10% of the nominal wall thickness on one-half inch casing. The optimal spacing will vary depending on the minimum size of flaws desired to be detected and the thickness of the casing. This optimal spacing may be readily determined by experimentation for any combination of these parameters. The magnetic detection transducers 56 generate a voltage in response to magnetic flux. As will be described later, when the flaw detection apparatus is in operation, these transducers detect the magnetic flux perturbations caused by longitudinal flaws in casing 10.

Wear plates 60 are mounted to the ends of the two legs of core 57. These plates 60 are preferably made of a hard non magnetic material having some lubricity, such as brass, beryllium copper, "Teflon", an oil impregnated porous material such as "Oilite", or other known bearing materials. These plates ride on the surface of casing 10 when electric solenoid 42 has been energized to force the magnetizing-detection units against the casing surface. Wear plates 60 prevent the steel core 57 from damaging the surface of the casing and vice-versa.

In operation, electric solenoid 42 is energized to force magnetizing-detection unit 45 into contact with the casing 10 to be inspected. Electric power is supplied to coil 55 from an external source through slip rings 37 (FIG. 1). Coil 55 may be supplied with either direct or alternating current. For an alternating current coil, adjusting the frequency of the current will change the sensitivity of the apparatus. Thus the frequency may be adjusted to optimize defect sensitivity for a particular type of casing. For direct current coils, defect sensitivity is optimized by adjusting the rotational speed of the apparatus by varying the speed of the motor. Upon energization of coil 55, a magnetic field will be generated as indicated in FIG. 3 by magnetic flux lines 61 (dotted lines). The magnetic field passes through the casing along a generally circumferential path between the two legs of core 57. Magnetic detection transducers 56 are arranged between the poles of the magnetic yoke so that any perturbations in the magnetic field resulting from longitudinal flaws in casing 10 will be detected by the transducers.

In an alternative embodiment, the apparatus may be constructed with a simple transducer support in place of magnetizing yoke 57. In operations using such an apparatus, a residual field would be produced in the casing by known techniques for generating circular magnetic fields in tubular members, e.g. placing a conductor through the bore of the tubular member and running a high current through that conductor for a short period of time. After generation of such a residual field in the casing, operations would be performed using the apparatus without the magnetizing yoke. Perturbations in the residual magnetic field resulting from longitudinal flaws would be detected by the magnetic detection transducers. Elimination of the magnetic yoke would reduce the mechanical load on the rotating portion of the apparatus.

Returning to FIG. 1, during operation of the flaw detection apparatus the magnetizing-detection units are moved over the surface of the casing by means of the arrangement of gears, clutch, and motor discussed above. Pinion gear 48 is fixedly attached to the output shaft of clutch 50. The input shaft of clutch 50 is driven by motor 52 through belt 51. Clutch 50 is preferably a magnetic or other type of clutch designed to slip when a certain torque level is reached. Pinion gear 48 acts through ring gears 47 to rotate outer support 40. The interaction of the threaded inner surface of outer support 40 and the threaded outer surface of support bracket 36 causes the magnetizing-detection units to move in a helical path about the longitudinal axis of the casing as outer support 40 is driven by the motor, clutch, and gear assembly. The threaded surfaces of outer support 40 and support bracket 36 are designed so that in each revolution about the casing, the path traced by the magnetizing-detection units will overlap the path traced during the previous revolution by approximately 10%. The direction of movement of the magnetizing-detection units may be reversed by reversing the direction of rotation of motor 52.

Limit switches 62 are mounted to the inner surface of frame 17 to prevent excessive axial movement of outer support 40, and to allow for automatic operations. The limit switches are mounted so as to be operable by contact with ring gears 47. When one of the ring gears 47 comes into contact with and operates a limit switch, the motor 52 is de-energized. Thus the apparatus may be energized with the magnetizing-detecting units at the beginning of the area to be inspected and left unattended, since rotation will automatically stop when the limit switch is operated. If the limit switch fails to de-energize motor 52, outer support 40 will continue to rotate until the ring gear contacts the limit switch body. When the torque limit of clutch 50 is reached, the clutch will begin to slip, thus stopping the movement of the outer support 40. This limits the possibility of damage to the apparatus and prevents the failure of motor 52.

The apparatus of the present invention locates substantially longitudinal flaws by detecting perturbations in the magnetic field, which perturbations have a component generally normal to the casing. An example of a perturbation caused by such a flaw is shown in FIGS. 4A and 4B. The magnetic field is graphically represented by magnetic flux lines 61 (only one line shown in FIG. 4). FIG. 4A shows a section taken through a casing 10 having a longitudinal flaw 65. Magnetic detection transducers 56a and 56b of magnetizing-detection unit 45 are shown positioned in proximity to casing 10 near the location of flaw 65. Magnetic flux line 61 generated by the magnetic yoke is diverted from its normal path by flaw 65. Flaw 65 creates a discontinuity in the permeability of the casing which causes this perturbation 61a in magnetic flux line 61. Perturbation 61a has a normal component 63a pointing out of the casing on one side of flaw 65 and a normal component 64a pointing into the casing on the other side of flaw 65. Corresponding horizontal components 63b and 64b of perturbation 61a are also shown in FIGS. 4A and 4B.

In FIG. 4A, magnetic detection transducer 56a is shown over the vicinity of the portion of perturbation 61a pointing out of the casing 10. This perturbation is detected by magnetic detection transducer 56a. Magnetic detection transducer 56a generates an output voltage proportional to component 63a of magnetic flux normal to and passing through the surface of the transducer. This output signal is amplified by electronic amplifier 46 (FIG. 1) and transmitted through slip rings 37 to an external indicating device.

In FIG. 4B, magnetic detection transducers 56a and 56b are shown centered over flaw 65. The perturbation 61a in magnetic flux line 61 is detected by both magnetic detection transducers 56a and 56b. It is important that the two transducers are mounted substantially equidistant from the surface of casing 10. The value of normal components 63a, 64a decrease with radial distance from the surface of casing 10. If the transducers are not substantially equidistant from the surface of the casing, one transducer will be less sensitive to flaws than the other, and erroneous results might be obtained.

Because one magnetic detection transducer is detecting component 63a of magnetic flux pointing out of the casing, and the other magnetic detection transducer is detecting component 64a of magnetic flux pointing into the casing, one transducer will generate a positive output voltage and the other transducer will generate a negative output voltage. In order to prevent these voltages from cancelling each other out, the voltages from the two detectors are differentially processed. In such processing, the negative output voltage is converted to a positive output voltage of equivalent magnitude. The two output voltages, both now positive, are summed to produce a final output signal. Such differential processing enhances the defect discrimination capabilities of the apparatus. The differential processing is carried out by electronic equipment external to this apparatus and not a part of the invention disclosed herein. Such differential processing devices are well known in the art.

Figure 5:
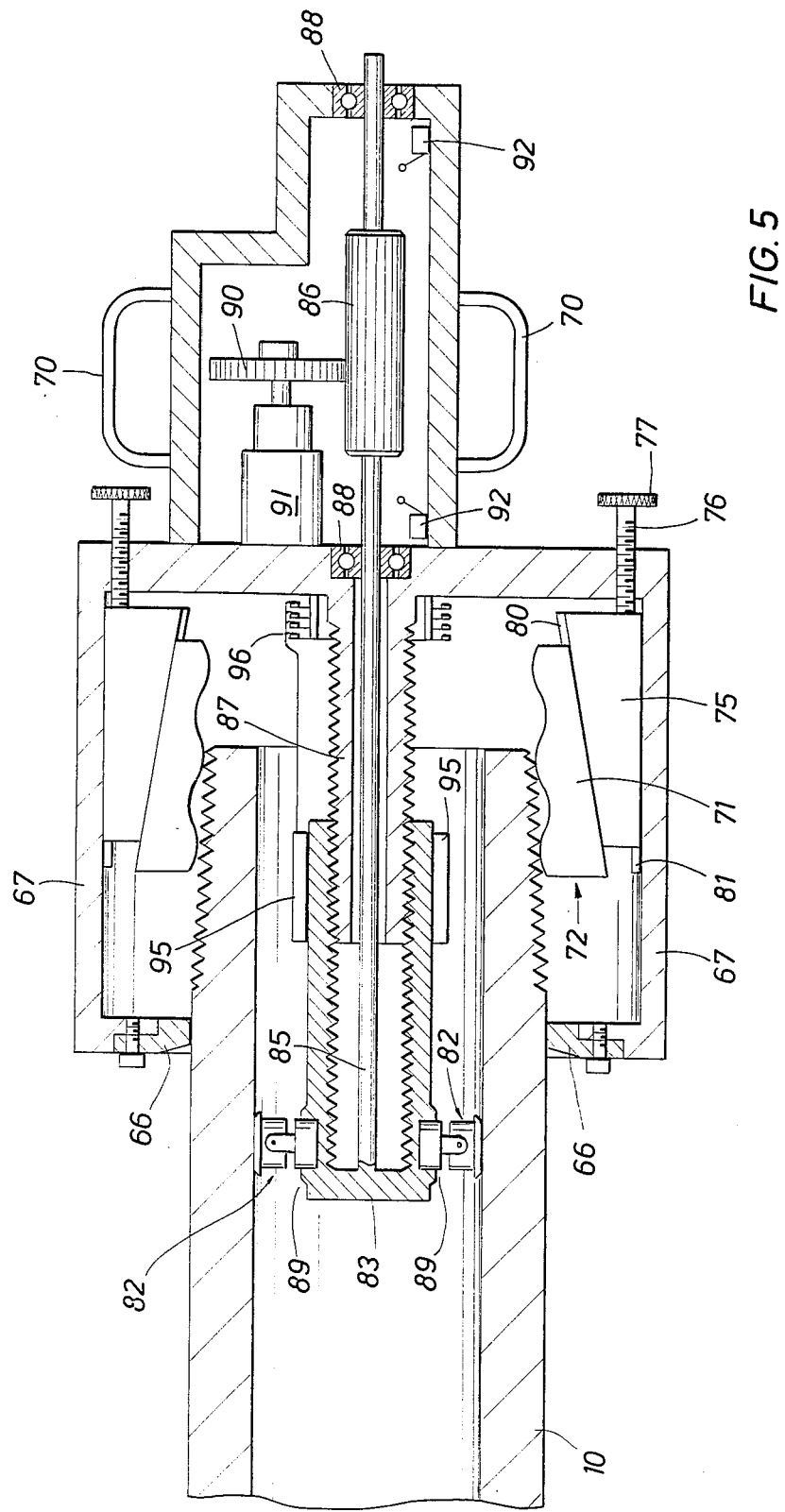
FIG. 5 is a sectional view of an alternate embodiment of the apparatus of the present invention mounted on a casing for inspection.

An alternate embodiment of the flaw detection apparatus of this invention is shown in FIG. 5. This alternate embodiment is designed primarily for detection of flaws along the inner surface of the end areas of tubular members. Like the preferred embodiment, this alternate embodiment of the flaw detection apparatus comprises magnetizing-detection units, means for moving said units about the surface of the tubular member, and means for centralizing and securing the apparatus on the tubular member. In this embodiment, the magnetizing-detection units are moved about the inner surface of the casing rather than about the outer surface as in the preferred embodiment.

The flaw detection apparatus is guided on to casing 10 by elastomeric guide 66 which is attached to main assembly frame 67. Handles 70 are provided to assist in handling the apparatus while inserting it onto casing 10. For flaw detection operations, the apparatus is pushed into casing 10 until the locking elements 71 of wedge block assemblies 72 come into contact with the outer surface of the casing.

Wedge block assemblies 72 act both as mechanical stops when inserting the apparatus into the casing and as securing means to lock the apparatus into place on the casing. Each wedge block assembly 72 comprises locking element 71, wedge block 75, threaded rod 76, wheel 77, and tracks 80 and 81. Locking element 71 is slideably mounted on track 80 on wedge block 75, and wedge block 75 is slideably mounted on track 81. Wheel 77 is fixedly attached to threaded rod 76.

To lock the inspection apparatus in place in casing 10, wheel 77 of each wedge block assembly 72 is rotated so as to thread rod 76 into frame 67. Threaded rod 76 pushes wedge block 75 along its track 81. Locking element 71 moves with wedge block 75 until the locking element is wedged against casing 10. As wheel 77 continues to be turned, wedge block 75 continues to slide along track 81. Locking element 71 now slides along track 80 as wedge block 75 forces locking element 71 against the surface of casing 10. This procedure is followed until all of the wedge block assemblies 72 have been tightened, locking the flaw detection apparatus in place in the casing.

Magnetizing-detection units 82 are similar to the magnetizing-detection units described for the preferred embodiment, as is the pivotable mounting from spring pistons 89. The operation of these units is also similar to that described for the preferred embodiment. As such, the design of the magnetizing-detection units, the mounting method for the units, and the details of operation of these units will not be described again. In this embodiment, the magnetizing-detection units are mounted from support element 83.

Support element 83 is a hollow cylindrical element having one closed end. The inner surface of the cylinder is threaded. Shaft extension 85 is fixedly attached at one end to the closed end of support element 83. Spline gear 86 is fixedly mounted on shaft extension 85. Shaft extension 85 is rotatably and slideably supported by bearings 88 mounted in frame 67.

Support shaft 87 is a tubular element having a threaded outer surface, and is rigidly mounted to frame 67. Support element 83 is threadedly mounted on support shaft 87, the threads on the inner surface of element 83 engaging with the threads on the outer surface of shaft 87. Shaft extension 85 runs through the bore of shaft 87. Spline gear 86 is connected through drive gear 90 to motor and clutch assembly 91.

In operation the motor and clutch assembly 91 acts through drive gear 90 to rotate spline gear 86. Rotation of spline gear 86 causes rotation of shaft extension 85 which, in turn, causes the rotation of support element 83. As support element 83 rotates, the threaded inner surface of support element 83 interacts with the threaded outer surface of support shaft 87 to cause the magnetizing-detection units 82 to move along a helical path over the inner surface of casing 10. Limit switches 92 are operated by contact with spline gear 86. Operation of either limit switch 92 will de-energize motor and clutch assembly 91 so as to prevent damage to the flaw detection apparatus.

The magnetizing-detection units 82 of this embodiment are similar in design and operation to the magnetizing-detection units 45 of the preferred embodiment of the present invention. During operation, the magnetizing-detection units are held in proximity to the surface of the casing to be inspected by an electric solenoid (not shown). During insertion or removal of the apparatus, the magnetizing-detection units are held off of the surface of the casing by spring pistons 89. The signals produced from the magnetizing-detection units are amplified by electronic amplifiers 95 mounted on support element 83. These signals are then transmitted to external conditioning and recording apparatus through slip rings 96.

It will be apparent that various changes may be made in details of construction from those shown in the attached drawings and discussed in conjunction therewith without departing from the spirit and scope of this invention as defined in the appended claims. For example, the apparatus and method can be used to detect flaws in the end area of any tubular member, regardless of the specific application. It is therefore to be understood that this invention is not to be limited to the specific details shown and described.

What we claim is:

1. Apparatus for detecting substantially longitudinal flaws in the end area of a tubular member comprising:
   means for generating a magnetic field in a generally circumferential direction through a portion of the end area of said tubular member;
   means positioned a spaced radial distance from the maximum material limit of said tubular member for sensing perturbations in the magnetic field in the region of any said substantially longitudinal flaws by detecting the component of the magnetic field normal and external to the surface of the tubular member, which sensing means produces a signal indicative of said normal component of the magnetic field, said sensing means being free from engagement of any threads present on said tubular member;
   means for supporting and moving said generating and sensing means along a generally helical path about the longitudinal axis of the end area of the tubular member being inspected, said supporting and moving means being free from engagement of any threads present on said tubular member;
   means for pivotably mounting said means for generating a magnetic field and said means for sensing perturbations to allow for movement over tapered or straight surfaces on said tubular member;
   means for centralizing and securing the apparatus on the end of the tubular member being inspected; and
   a frame from which said supporting and moving means and said centralizing and securing means are supported;
   whereby a magnetic perturbation is created around the substantially longitudinal flaws in said tubular member and the sensing means detects said perturbations as the generating and sensing means are moved along said helical path over said flaws.

2. The apparatus recited in claim 1 wherein said means for sensing perturbations comprises two Hall elements.

3. The apparatus recited in claim 2 wherein said Hall elements are mounted equidistant from the outer surface of said tubular member such that a surface passing through the surface of each of the two Hall elements is substantially concentric to the surface of the tubular member, said Hall elements further being spaced apart, and being aligned such that the line passing through the center line of both Hall elements is substantially perpendicular to the longitudinal axis of said tubular member.

4. The apparatus recited in claim 1 further comprising:
   means for moving said means for generating a magnetic field and said means for sensing perturbations into proximity with the surface of the tubular member before inspection; and
   means for moving said means for generating a magnetic field and said means for sensing perturbations away from the surface of the tubular member when said inspection is completed.

5. The apparatus recited in claim 1 wherein said means for generating a magnetic field comprises a generally U-shaped steel core having a coil wrapped about the portion of the core between the two legs of the core.

6. The apparatus recited in claim 5 further comprising wear plates mounted on the portion of said core proximate to the surface of the tubular member to prevent said core from damaging the surface of said tubular member during inspection.

7. The apparatus recited in claim 1 wherein said means for generating a magnetic field comprises a generally U-shaped permanent magnet.

8. The apparatus recited in claim 1 further comprising electronic amplifiers to amplify the signal produced by said means for sensing perturbations.

9. The apparatus recited in claim 1 further comprising slip rings through which the signal produced by said means for sensing perturbations is transmitted to an external indicating device, and through which power is supplied to the means for generating a magnetic field and the means for sensing perturbations.

10. The apparatus recited in claim 1 wherein said means for generating a magnetic field and said means for sensing perturbations are mounted so as to be exterior to said tubular member when said apparatus is secured to said tubular member.

11. The apparatus recited in claim 1 wherein said means for generating a magnetic field and said means for sensing perturbations are mounted so as to be interior to said tubular member when said apparatus is secured to said tubular member.

12. The apparatus recited in claim 1 wherein said means for supporting and moving said generating and sensing means comprises:
   a cylindrical support bracket having a threaded outer surface, said bracket being fixedly mounted to the frame;
   a cylindrical outer support having a threaded inner surface, which surface is engaged with the threaded outer surface of said support bracket;
   a plurality of ring gears mounted to the outer surface of said outer support;
   a pinion gear rotatably mounted in the frame so as to engage said ring gears;
   a clutch having an input shaft and an output shaft, said output shaft being fixedly attached to said pinion gear;
   a reversible electric motor fixedly mounted o said frame, said motor having a shaft; and
   a drive belt connecting the shaft of said motor and the input shaft of said clutch;
   whereby said motor operates through said belt, clutch, pinion gear, and ring gears to rotate said outer support.

13. Apparatus for detecting substantailly longitudinal flaws in the end area of a tubular member comprising:
   means for centralizing and securing the apparatus on the end of the tubular member being inspected;
   means for generating a localized magnetic field in a generally circumferential direction through a portion of the end area of said tubular member;
   means positioned a spaced radial distance from the maximum material limit of said tubular member for sensing perturbations in said magnetic field by detecting the component of the magnetic field normal and external to the surface of the tubular member in the general vicinity of any substantially longitudinal flaws in said tubular member, which sensing means produces a signal indicative of said normal component of the magnetic field, said sensing means being free from engagement of any threads present on said tubular member;

means for moving said generating and sensing means into proximity with the surface of the tubular member before inspection;

means for moving said generating and sensing means away from the surface of the tubular member when said inspection is completed;

means for pivotably mounting said generating and sensing means whereby said pivotable mounting allows said means to remain proximate to either tapered or straight surfaces on said tubular member;

means for supporting and moving said generating and sensing means along a generally helical path about the longitudinal axis of the end area of the tubular member being inspected, said supporting and moving means being free from engagement of any threads present on said tubular member; and a frame from which said supporting and moving means and said centralizing and securing means are supported;

whereby a magnetic perturbation is created around the substantially longitudinal flaws in said tubular member and the sensing means detects said perturbations as the generating and sensing means are moved along said helical path over said flaws.

14. The apparatus recited in claim 13 wherein said means for sensing perturbations comprises two Hall elements.

15. The apparatus recited in claim 14 wherein said Hall elements are mounted equidistant from the outer surface of said tubular member such that a surface passing through the surface of each of the two Hall elements would be substantially concentric to the surface of the tubular member, said Hall elements further being spaced apart, and being aligned such that the line passing through the center line of both Hall elements is substantially perpendicular to the longitudinal axis of said tubular member.

16. The apparatus recited in claim 13 wherein said means for generating a magnetic field comprises a generally U-shaped steel core having a coil wrapped about the portion of the core between the two legs of the core.

17. The apparatus recited in claim 16 further comprising wear plates mounted on the portion of said core proximate to the surface of the tubular member to prevent said core from damaging the surface of said tubular member during inspection.

18. The apparatus recited in claim 13 wherein said means for generating a magnetic field comprises a generally U-shaped permanent magnet.

19. The apparatus recited in claim 13 further comprising electronic amplifiers to amplify the signal produced by said means for sensing perturbations.

20. The apparatus recited in claim 13 further comprising-slip rings through which the signal produced by said means for sensing perturbations is transmitted to an external indicating device, and through which power is supplied to the means for generating a magnetic field and the means for sensing perturbations.

21. The apparatus recited in claim 13 wherein said means for generating a magnetic field and said means for sensing perturbations are mounted so as to be exterior to said tubular member when said apparatus is secured to said tubular member.

22. The apparatus recited in claim 13 wherein said means for generating a magnetic field and said means for sensing perturbations are mounted so as to be interior to said tubular member when said apparatus is secured to said tubular member.

23. The apparatus recited in claim 13 wherein said means for supporting and moving said generating and sensing means comprises:

a cylindrical support bracket having a threaded outer surface, said bracket being fixedly mounted to the frame;

a cylindrical outer support having a threaded inner surface, which surface is engaged with the threaded outer surface of said support bracket;

a plurality of ring gears mounted to the outer surface of said outer support;

a pinion gear rotatably mounted in the frame so as to engage said ring gears;

a clutch having an input shaft and an output shaft, said output shaft being fixedly attached to said pinion gear;

a reversible electric motor fixedly mounted to said frame, said motor having a shaft; and a drive belt connecting the shaft of said motor and the input shaft of said clutch;

whereby said motor operates through said belt, clutch, pinion gear, and ring gears to rotate said outer support.

24. Apparatus for detecting substantially longitudinal flaws in the end area of a tubular member on which a circumferential residual magnetic field has been imparted, comprising:

means for centralizing and securing the apparatus on the end of the tubular member being inspected;

means positioned a spaced radial distance from the maximum material limit of said tubular member for sensing perturbations in said magnetic field by detecting the component of the magnetic field normal and external to the surface of the tubular member in the general vicinity of any substantially longitudinal flaws in said tubular member, which sensing means produces a signal indicative of said normal component of the magnetic field, said sensing means being free from engagement of any threads present on said tubular member;

means for moving said sensing means into proximity with the surface of the tubular member before inspection;

means for moving said sensing means away from the surface of the tubular member when said inspection is completed;

means for pivotably mounting said sensing means whereby said pivotable mounting allows said means to remain proximate to either tapered or straight surfaces on said tubular member;

means for supporting and moving said sensing means along a generally helical path about the longitudinal axis of the end area of the tubular member being inspected, said supporting and moving means being free from engagement of any threads present on said tubular member; and a frame from which said supporting and moving means and said centralizing and securing means are supported;

whereby the magnetic perturbations created by said residual magnetic field around the substantially longitudinal flaws in said tubular member are detected by said sensing means as said sensing means moves along said helical path over said flaws.

25. Apparatus for detecting substantially longitudinal flaws in the end area of a tubular member comprising:

means for centralizing and securing the apparatus on the end of the tubular member being inspected;

a generally U-shaped steel core having a coil wrapped about the portion of the core between the two legs of the core for generating in combination with said core a localized magnetic field in a generally circumferential direction through a portion of the end of said tubular member;

two Hall elements positioned between the legs of said core, a spaced radial distance from the maximum material limit of said tubular member, which Hall elements sense perturbations in said magnetic field by detecting the component of the magnetic field normal and external to the surface of the tubular member in the general vicinity of any substantially longitudinal flaws in said tubular member, and produce a signal indicative of said normal component of the magnetic field, said Hall elements and said steel core being free from engagement of any threads present on said tubular member;

an electric solenoid for moving said steel core and sensing means into proximity with the surface of the tubular member before inspection;

spring pistons for moving said steel core and sensing means away from the surface of the tubular member when said inspection is completed;

means for pivotably mounting said core, coil and Hall elements whereby said pivotable mounting allows said core, coil and Hall elements to remain proximate to either tapered or straight surfaces on said tubular member;

means for supporting and moving said steel core, coil and Hall elements along a generally helical path about the longitudinal axis of the end area of the tubular member being inspected, said means being free from engagement of any threads present on said tubular member; and a frame from which said supporting and moving means and said centralizing and securing means are supported;

whereby a magnetic perturbation is created around the substantially longitudinal flaws in said tubular member and the Hall elements detect said perturbations as the steel core, coil and sensing means are moved along said helical path over said flaws.

26. The apparatus recited in claim 25 wherein said Hall elements are mounted equidistant from the outer surface of said tubular member such that a surface passing through the surface of each of the two Hall elements would be substantially concentric to the surface of the tubular member, said Hall elements further being spaced apart, and being aligned such that the line passing through the center line of both Hall elements is substantially perpendicular to the longitudinal axis of said tubular member.

* * * * *